United States Patent
Nastasi

(10) Patent No.: US 11,850,403 B2
(45) Date of Patent: Dec. 26, 2023

(54) SYRINGES AND MEDICAL DEVICES WITH WINDOWED LABELS

(71) Applicant: Nicholas Nastasi, Sickerville, NJ (US)

(72) Inventor: Nicholas Nastasi, Sickerville, NJ (US)

( * ) Notice: Subject to any disclaimer, the term of this patent is extended or adjusted under 35 U.S.C. 154(b) by 124 days.

(21) Appl. No.: 17/243,402

(22) Filed: Apr. 28, 2021

(65) Prior Publication Data

US 2022/0347389 A1 Nov. 3, 2022

(51) Int. Cl.
*A61M 5/31* (2006.01)

(52) U.S. Cl.
CPC ... *A61M 5/3129* (2013.01); *A61M 2005/3125* (2013.01); *A61M 2205/59* (2013.01); *A61M 2205/6063* (2013.01)

(58) Field of Classification Search
CPC ........ A61M 5/3129; A61M 2005/3125; A61M 2205/59; A61M 2205/6063
See application file for complete search history.

(56) References Cited

U.S. PATENT DOCUMENTS

| | | |
|---|---|---|
| D496,405 S | 9/2004 | Stewart et al. |
| D500,342 S | 12/2004 | Stewart et al. |
| D500,524 S | 1/2005 | Stewart et al. |
| D503,197 S | 3/2005 | Stewart et al. |
| D521,565 S | 5/2006 | Stewart et al. |
| 8,182,450 B2 | 5/2012 | Moosheimer et al. |
| 8,377,007 B2 | 2/2013 | Moosheimer et al. |
| 9,085,402 B2 | 7/2015 | Key |
| 9,248,243 B2 | 2/2016 | Schreiner et al. |
| 9,687,947 B2 | 6/2017 | Roehm et al. |
| D881,392 S | 4/2020 | Pujara et al. |
| 10,661,935 B2 | 5/2020 | McKinnon et al. |
| 10,716,734 B2 | 7/2020 | Williams et al. |
| D895,110 S | 9/2020 | Takada et al. |
| 10,803,372 B2 | 10/2020 | Ramzan et al. |
| 10,807,340 B2 | 10/2020 | Karan |
| 10,821,233 B2 | 11/2020 | Hutchinson et al. |
| 10,836,938 B2 | 11/2020 | Karhu et al. |
| 10,842,940 B1 | 11/2020 | Pusateri |
| 10,889,423 B2 | 1/2021 | Shadle |

(Continued)

FOREIGN PATENT DOCUMENTS

JP 2003275307 A * 9/2003

OTHER PUBLICATIONS

"All the Pre Cut Syringe Labels and Label Tape You Need in One Place," Sharn Anesthesia Inc. Website, Available Online at https://www.sharn.com/anesthesia-essentials/c/syringe-labels/, Available as Early as Apr. 19, 2016, 2 pages.

(Continued)

*Primary Examiner* — Lauren P Farrar
(74) *Attorney, Agent, or Firm* — J. Douglas Wells; McCoy Russell LLP

(57) ABSTRACT

A syringe or medical device, especially adapted and suited for use with children, having a label with non-transparent and transparent portions positioned on the syringe or medical device so as to avoid covering measurement graduations or indicia needed by a medical practitioner for performing a medical procedure, such as an injection or blood collection, and using attention grabbing graphic images on the non-transparent portion of the label for distracting the patient's attention from fluids and/or hypodermic needles involved in the medical procedure.

9 Claims, 4 Drawing Sheets

(56) References Cited

U.S. PATENT DOCUMENTS

| | | | | |
|---|---|---|---|---|
| 2005/0209567 A1* | 9/2005 | Sibbitt | ............... | A61B 42/00 604/80 |
| 2008/0139076 A1* | 6/2008 | Frasier-Scott | ......... | A61M 5/14 446/72 |
| 2013/0043157 A1* | 2/2013 | Key | ..................... | B65D 85/00 206/459.1 |
| 2017/0361026 A1* | 12/2017 | Eldawud | ............. | A61M 5/326 |

OTHER PUBLICATIONS

"Syringe Labels—Shop premium-quality medical syringe labels," International Lab Tag Website, Available Online at https://www.labtag.com/shop/category/labels/healthcare-labels/syringe-labels/, Available as Early as Sep. 27, 2020, 2 pages.

"Drug Syringe Labels & Tapes," United Ad Label Website, Available Online at https://www.unitedadlabel.com/veterinary/medication-dispensing-labels/drug-syringe-labels-tapes, Available as Early as Sep. 27, 2020, 5 pages.

"Single & Two Panel Label Services," Patheon Website, Available Online at https://patheon.com/clinical-trial-services/clinical-label-services/single-two-panel-label-services/, Available as Early as Oct. 21, 2020, 2 pages.

"BLANK Drug Syringe Stickers," Veterinary Apparel Website, Available Online at https://www.veterinaryapparel.com/product/2090/blank-drug-syringe-stickers, Retrieved on Apr. 9, 2021, 2 pages.

"Syringe Stickers: What Makes Them Unique?," Shamrock Labels Website, Available Online at https://www.shamrocklabels.com/syringe-stickers-what-makes-them-unique/, Retrieved on Apr. 9, 2021, 3 pages.

"Syringe Labels," Sheet Labels Website, Available Online at https://www.sheetlabels.com/markets/medical-labels/syringe-labels, Retrieved on Apr. 9, 2021, 11 pages.

* cited by examiner

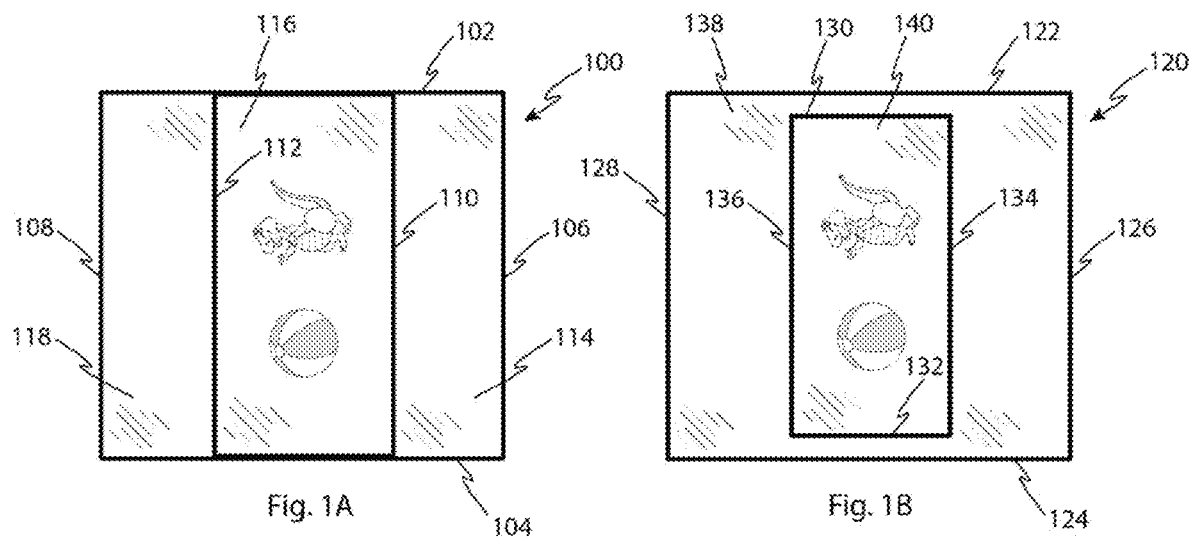
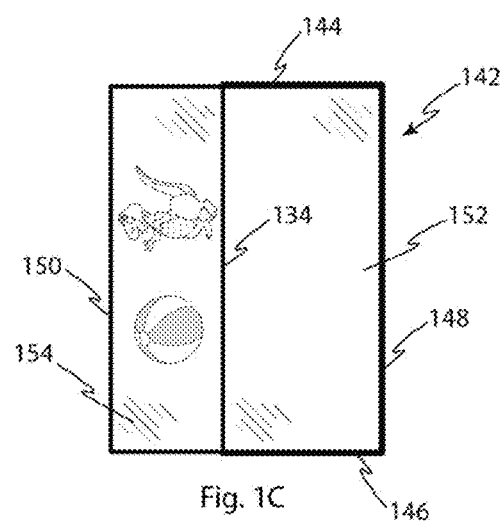

SYRINGES AND MEDICAL DEVICES WITH WINDOWED LABELS

FIELD

Embodiments of the subject matter disclosed herein relate to syringes and medical devices with windowed labels, or labels that enable indicia or other marks, text, impressions, or images to be printed or affixed on or to the label with one or more perimeter or area that is clear or transparent so as to permit visually reading graduations and/or indications on the underlying medical device such as a hypodermic needle syringe or other intravenous fluid handling medical device.

BACKGROUND

Medical products may comprise a label adhered to a label liner from which the label is removed and then adhered to a package, for example a medicine bottle. By way of example, the label may be applied to the medicine bottle by first adhering a first edge of (usually the shorter dimension of) the (typically rectangular shaped) label and rotating the bottle and/or wrapping the label onto the bottle progressively from the first edge, firmly pressing the label to ensure full adhesion of the label to the bottle. Such labels are commonly used with pharmaceuticals. However, medical devices such as hypodermic needle syringes, syringes and needles used for injections or blood collection or other medical procedures may benefit by the use of labels, and existing applications comprise blank labels or blank drug syringe stickers, such peel and stick syringe stickers designed to help with identification of special instructions, identification of specific drugs, or identification and tracking of patients, clients, and/or medical practitioners.

Adults may readily appreciate the benefits of the "shots" that once were (or still are) dreaded or feared, when, as children, such "shots" were given by a medical practitioner. The physical discomfort may comprise an initial jab with a lingering bee sting like pain. For adults, the discomforts may be cognitively determined to be outweighed by the benefits of the injection. Children, however, may be much less easily convinced and may often exhibit substantial anxiety with any procedure involving hypodermic needles, or sharps, or medical devices adapted for hypodermic injections or collection of bodily fluid (such as blood), or devices involving intravenous (IV) bags, metering, tubes, and delivery sites on and in the body. Medical practitioners often struggle to address the apprehensions and/or anxiety and/or fear of non-adult (e.g., child) patients or those with greater apprehension as to the use of such devices for delivering and/or collecting fluids, especially via hypodermic needle syringes, and especially where the patient may easily view the extraction of blood or introduction of the substance being injected, including movement of the syringe plunger seal, for example.

However, heretofore efforts directed to improved labeling of such medical devices have been limited to addressing the needs of proper identification for the medical practitioner, for example, to help ensure the solution in the syringe is properly administered. One such solution comprises preprinted syringe stickers that contain identification related information such as the type of drug being administered—i.e., name of medication/substance, medication strength/concentration, date of preparation of the substance, and instructions as to safe storage. Such information provides helpful indication of what's being administered, how much is to be used, the age of the batch or lot of the medication, and whether, for example, refrigerated storage or cryogenic freezing is required.

One particular solution comprises a syringe sticker that consists of a rectangular sticker with some or all of the aforementioned information typed or written on particular lines on the sticker, with the sticker applied to a portion of the syringe body. Another solution comprises a syringe sticker that wraps around the circumference of the syringe body near the T-end (barrel flange) or plunger (plunger seal) insertion end of the syringe longitudinally opposite to the needle end/fluid moving end of the syringe, and forming a flag extending radially outward from the syringe body. The flag surfaces of the label then provide area for the aforementioned identification and usage related medical/medication information.

None of the existing labeling methods and/or existing labels, however, address the aforementioned issues regarding using such medical devices with children or patients with potentially heightened anxiety and/or discomfort with medical procedures involving delivery or collection of fluids from the body, especially when such procedures may be in plain view of the patient. What is needed, therefore, are products and method that address the aforementioned and other shortcomings and problems.

BRIEF DESCRIPTION

Embodiments of the present disclosure relate generally to a label(s) and process(es) that enable (preferably attention grabbing) indicia or other marks, text, impressions, or images to be printed or affixed to the label and with one or more perimeter material that is clear or transparent on at least a portion of the label, and in particular, a label or labels fabricated from different materials wherein the a portion of the label is of material that permits the indicia or other marks, text, impressions or images to be non-transparent while the outer perimeter or other sections of the label is/are transparent or translucent; and the label includes a partial or full bottom surface comprising an adhesive for affixing the label or labels to a surface of an object/medical device and having the transparent or translucent area permitting the observer/medical practitioner to view graduations or other measurement markings, or other makings on the medical device, to which the label or labels are affixed to, that aid the medical practitioner in effectively using/operating the medical device.

The present disclosure comprises syringes and medical devices with windowed labels, or labels that enable (preferably attention getting and/or patient distracting) indicia or other marks, text, impressions, or images to be printed or affixed on or to the label with one or more perimeter or area that is clear or transparent (i.e., windowed) so as to permit (the medical practitioner) visually reading graduations and/or indications on the underlying medical device such as a hypodermic needle syringe or other intravenous fluid handling medical device. The printable portion of the label preferably comprises an opaque area that includes graphical images designed to capture the attention of the patient/subject of the medical procedure involving the labeled medical device and also at least partially (divert the patient's attention away from the hypodermic needle and) obscure view of fluid beneath/behind the opaque portion (i.e., within the syringe interior) and view of the plunger seal and movement of the plunger seal and change in the amount of fluid within the syringe/medical device.

Embodiments of the labels preferably comprise the aforementioned opaque/non-transparent and windowed/transparent portions, with an adhesive backing. Preferred embodiments comprise labels of a generally rectangular shape and sized and adapted so that an opaque/non-transparent portion having an attention grabbing graphical image thereon is positionable on the medical device in an area of the medical device free of graduations or other markings required by the medical practitioner for safe and effective operation of the medical device (such as, for example, the administering of a measured substance such as a vaccine or the collection of an amount of bodily fluid such as blood); the label is preferably wrapped around the circumference of the medical device (such as a syringe) in such fashion that the non-transparent portion of the label extends toward the needle end away from and longitudinally opposite, for example, the T-end of the syringe where the plunger (plunger seal) is inserted, so that the non-transparent portion of the label at least partially obscures the patient's view of fluid within (and plunger seal movement and change of fluid amount) the portion of the device (e.g., syringe) nearest the needle and plunger seal end of travel toward the needle end.

By using such syringes and medical devices with windowed labels, the attention of the patient may be averted from the medical procedure itself (e.g., using a hypodermic needle) and, at least temporarily and at least partially, directed toward attention grabbing, emotionally positive/stimulating (e.g., playful and/or happy and/or kid/child-themed) graphics positioned on a non-transparent portion of the device label, thereby at least partially and at least temporarily alleviating patient anxiety and/or apprehension as the particular medical procedure is being performed.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The accompanying drawings are incorporated herein as part of the specification. The drawings described herein illustrate embodiments of the presently disclosed subject matter, and are illustrative of selected principles and teachings of the present disclosure. However, the drawings do not illustrate all possible implementations of the presently disclosed subject matter, and are not intended to limit the scope of the present disclosure in any way. The above, as well as other advantages of the present disclosure will become readily apparent to those skilled in the art from the following detailed description when considered in the light of the accompanying drawings.

FIG. 1A illustrates a top view of a label or sticker applicable onto medical devices or other object, whereby a strip of non-transparent material (having attention grabbing, kid-themed images thereon) is positioned between two narrower areas of transparent material, according to one embodiment.

FIG. 1B illustrates a top view of a label or sticker applicable onto medical devices or other object, whereby an area of non-transparent material (with attention grabbing images thereon) is surrounded by areas of transparent material along the perimeter of the non-transparent area, according to one embodiment.

FIG. 1C illustrates a top view of a label or sticker applicable onto medical devices or other object, whereby a strip of non-transparent material (having attention grabbing images thereon) is side-by-side with an area of transparent material, according to one embodiment.

FIGS. 4-7 include illustration of features which, according to various embodiments, are depicted to be approximately proportionate with one another.

DETAILED DESCRIPTION

It is to be understood that embodiments of the present disclosure may assume various alternative orientations and step sequences, except where expressly specified to the contrary. It is also to be understood that the assemblies, devices, and methods illustrated in the attached drawings, and described in the following specification are simply exemplary embodiments of the inventive concepts. Hence, specific dimensions, directions, or other physical characteristics relating to the embodiments disclosed, if any, are not to be considered as limiting, unless expressly stated otherwise.

The present inventor discovered a syringe or medical device with a windowed label, the label having a non-transparent area with attention grabbing graphics thereon and a transparent area enabling any graduations or markings upon which the label is affixed to be easily viewed by the medical practitioner using the syringe or medical device. The present inventor discovered an unmet need for structures and methods adapted for distracting the patient, particularly children or others with apprehension and anxiety toward procedures using hypodermic needle syringes and the like, so as to aid the medical practitioner safely administer the injection or blood draw (or other medical procedure) while at the same time calm and reassure the patient. The present inventor particularly discovered that incorporating positive themed, or fun/happy/upbeat, attention grabbing graphical images on the medical device, positioned so as to at least partially obscure the fluid being injected or the blood being drawn, and so as to at least partially obscure the position and/or movement of the syringe plunger seal (and change in the amount of fluid within the syringe), provides a distractive feature to the medical device and the medical procedure being performed. The present inventor determined that healthcare workers are particularly interested in the calming, attention grabbing aspects of the described embodiments, as well as the low cost and ease of use of such embodiments.

Figure 2A:
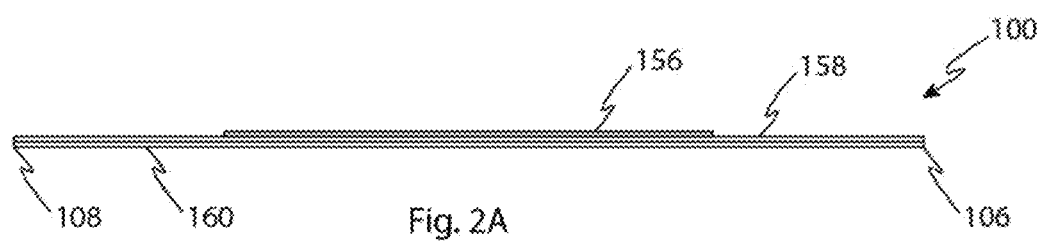
FIG. 2A illustrates a cross-section of the label or sticker shown in FIG. 1A, whereby the strip of non-transparent material is on top of a layer of transparent material, or the strip of non-transparent material is adjacent to areas of transparent material on each of two parallel sides, according to embodiments.
Figure 2B:
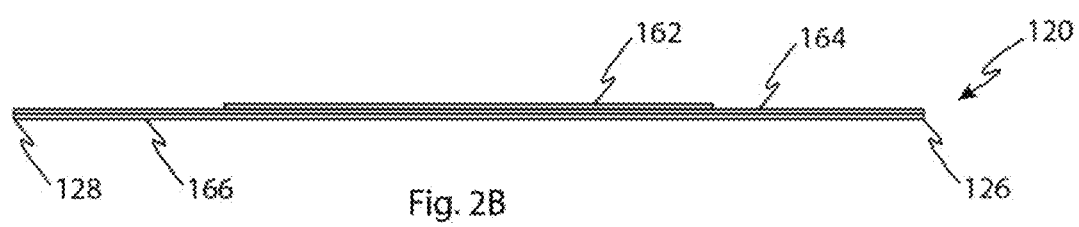
FIG. 2B illustrates a cross-section of the label or sticker shown in FIG. 1B, whereby the area of non-transparent material is on top of a layer of transparent material, or the area of non-transparent material is set within areas of transparent material about the perimeter of the area of non-transparent material, according to embodiments.
Figure 2C:
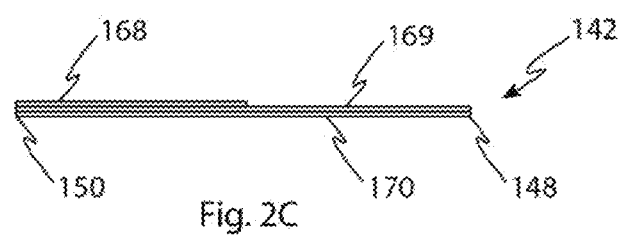
FIG. 2C illustrates a cross-section of the label or sticker shown in FIG. 1C, whereby the strip of non-transparent material is on top of a layer of transparent material, or the strip of non-transparent material is adjacent to the area of transparent material, according to embodiments.
Figure 3A:
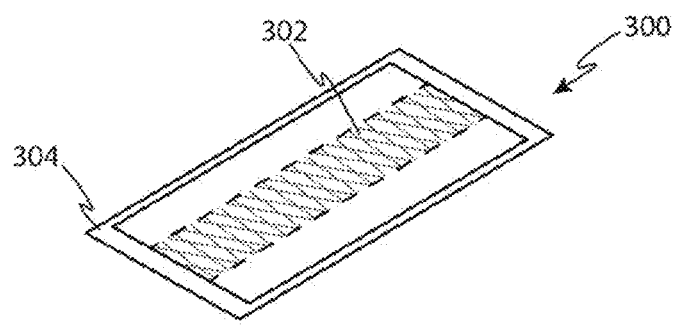
FIG. 3A shows a perspective view of a label, or pre-cut label, positioned upon a label liner, which may be arranged in a sheet of multiple columns and rows or in a tape/reel manner, or otherwise, wherefrom individual labels may be removed for subsequent application to a syringe body or other medical device, according to embodiments.
Figure 3B:
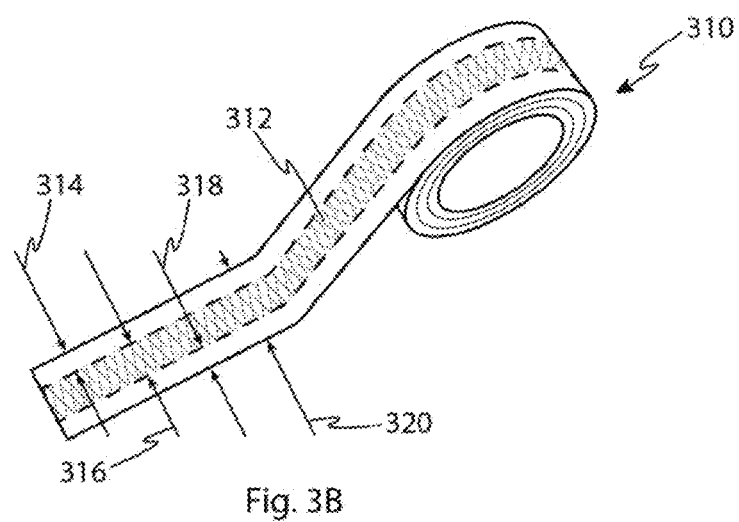
FIG. 3B shows a label tape, whereby labels comprise a continuous repeating pattern/sequence of graphic images, and whereby labels of varying length may be cut/ripped for subsequent application to syringes or other medical devices of differing longitudinal lengths, according to embodiments.
Figure 4:
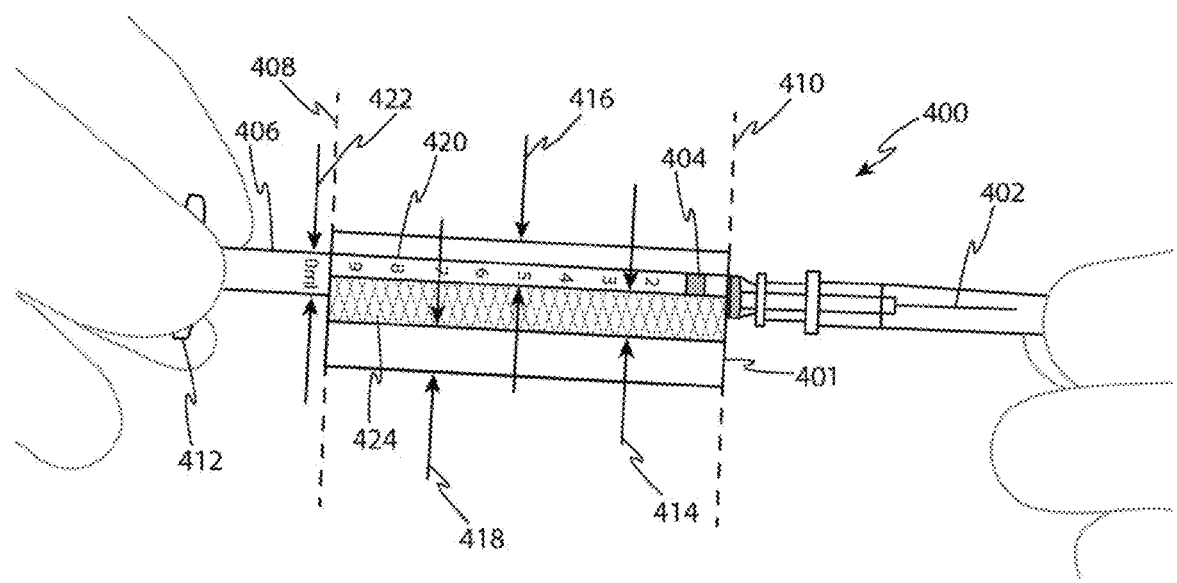
FIG. 4 illustrates a medical practitioner holding a syringe with a label as shown in FIG. 1A in a position for adhering to the syringe such that the non-transparent portion of the label is aligned so as not to obscure graduations running longitudinally lengthwise along the barrel (body) of the syringe, according to embodiments.
Figure 5:
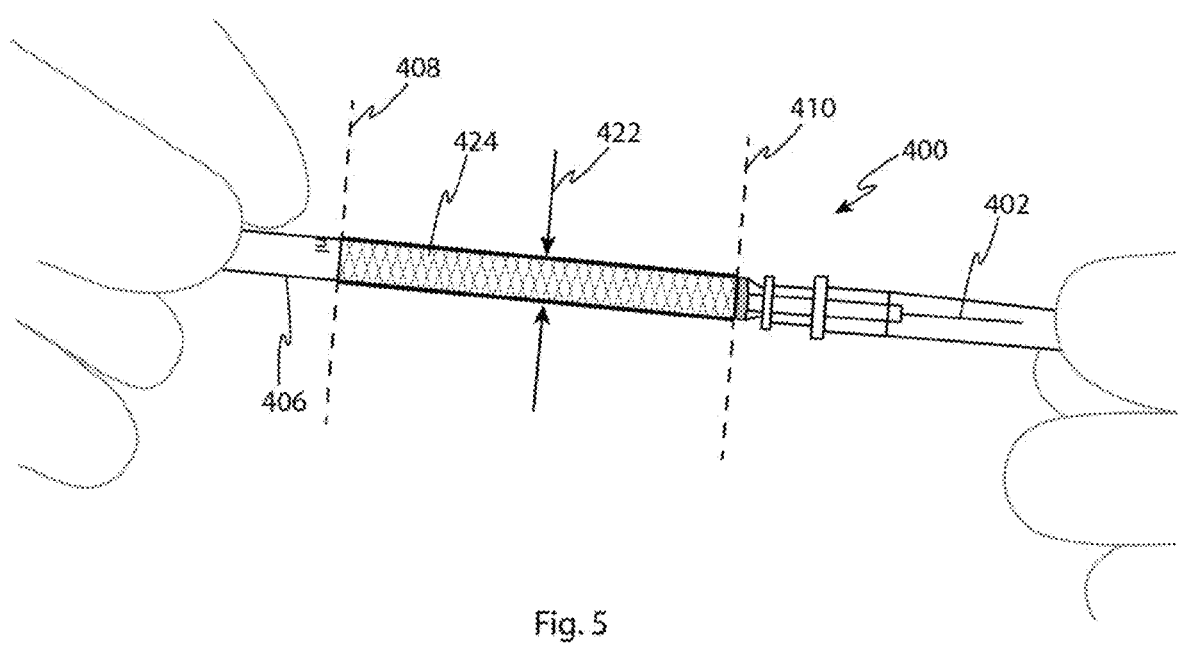
FIG. 5 illustrates the medical practitioner in FIG. 4 holding the syringe with the label fully applied to the syringe body and with the syringe rotated (with respect to FIG. 4) to depict the non-transparent strip of the label facing the viewer, so as to hide the interior of the syringe and so as to hide the position and movement of the plunger seal, according to embodiments.
Figure 6:
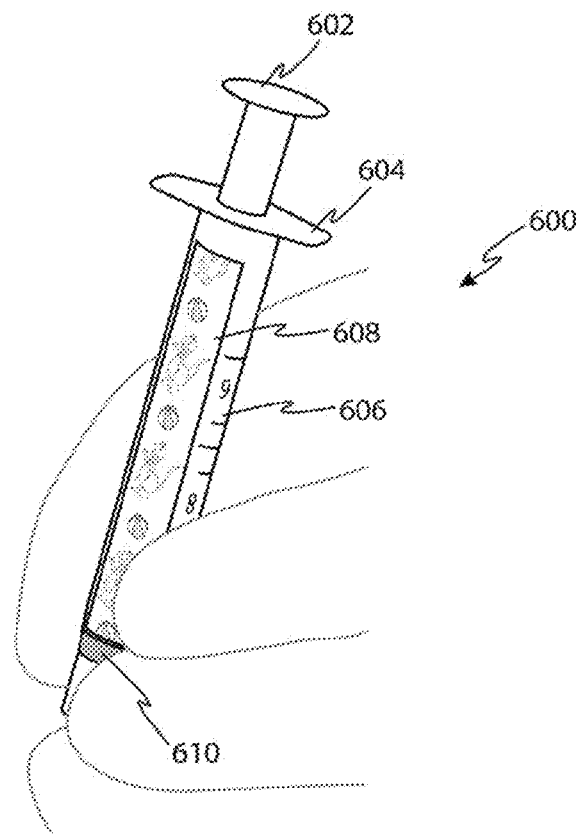
FIG. 6 shows a medical practitioner holding a differently dimensioned syringe having an applied label comprising a label as shown in FIG. 1A or 1C, according to embodiments.
Figure 7:
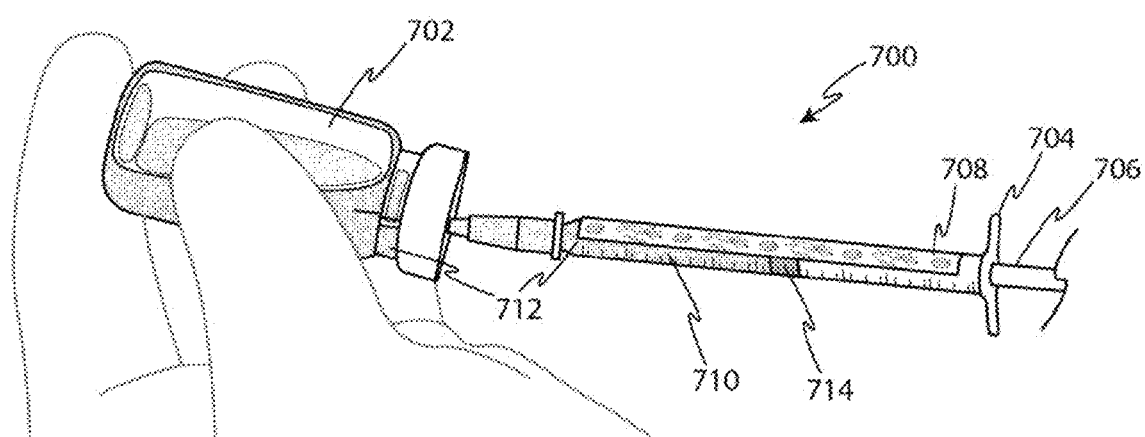
FIG. 7 shows a medical practitioner holding a vial from which fluid has been drawn into the interior volume of a syringe, whereby a label as in FIG. 1A or 1C is applied to the syringe body, thereby obscuring (in the area covered by the non-transparent portion of the label) both the fluid within the syringe and the position of the syringe plunger seal, according to embodiments.

As an overview, the top views of FIGS. 1A, 1B, and 1C, and corresponding cross-sectional views in FIGS. 2A, 2B, and 2C, respectively, disclose exemplary label structures, according to various preferred embodiments. FIGS. 3A and 3B provide exemplary means for handling unapplied labels, according to preferred embodiments. FIGS. 4 and 5 illustrate applying an exemplary label to a hypodermic needle syringe (of the type commonly used for injections), according to embodiments. FIG. 6 illustrates a labelled hypodermic needle syringe of a different type than shown in FIGS. 4 and 5, that may be used for blood draw/blood sample collection procedures, according to one embodiment. And FIG. 7 illustrates a labelled hypodermic needle syringe (of the type shown in FIGS. 4 and 5) shown extracting serum from a vial, providing visual access to measurement graduations along the syringe body and also obscuring/hiding at least a portion of the interior fluid holding volume of the syringe and the relative position of (and movement of) the plunger seal within the syringe body (barrel), according to embodiments.

Turning now to the figures, FIG. 1A illustrates a top view of a label or sticker 100 applicable onto medical devices or other object, whereby a strip of non-transparent material 116 (having attention grabbing, kid-themed images thereon) is positioned between two narrower areas of transparent material 118, 114, according to one embodiment. The label 100 is preferably square or rectangular with dimensions sized and adapted such that the width of the non-transparent material 110-112 is less than the circumference of, for example, a syringe body (target) to which the label 100 is to be applied, and sufficiently less than the circumference including a portion of the circumference having measurement graduations (so that such graduations remain visible through one or both transparent portions 114, 118). The width of the transparent portions, 106-110 for portion 114 and 108-112 for portion 118, are preferably each less than the width 110-112 of the non-transparent/opaque portion 116. The longitudinal length 102-104 of the label 100 is preferably sized and adapted to the (target) syringe body so that the opaque portion 116 (and attention grabbing, kid-themed graphics printed/rendered thereon such as the one or more beach ball and one or more dinosaur shown) extends between the end of plunger seal travel nearest the needle end of the syringe body and near enough toward the T-end of the syringe body so as to obscure a longitudinal extent of the syringe body sufficient in lengthwise dimension to cover a normal operating range (longitudinal plunger seal travel).

The label 100, as shown in FIG. 1A, is preferably rectangular in shape, with a circumferential width 106-108 and a longitudinal length 102-104. The label 100 may be shaped differently. For example, the label, such as label 100, may be triangular, circular, or of an irregular or other shape, to, for instance, accommodate (or avoid covering) measurement graduations or other information on the target syringe body to remain visible (post label application). As another example, the label may be shaped so as to be applicable to irregularly shaped medical devices such as, for example, an IV bag or components thereof.

The graphical images shown in FIG. 1A is shown as one or more beach ball and one or more dinosaur, preferably in colors, textures, and orientations directed to generate a positive attention getting, calming emotional response from a child, or non-adult, or, in some embodiments, an individual patient generally. Other images can be used that are preferably designed so as to, again, generate a positive attention grabbing, calming emotional response, preferably targeted toward children, or in some embodiments, an individual patient generally. The range of potential images to include in the non-transparent portion, such as opaque portion 116, is limited only in terms of such images being chosen so as to generate the desired attention grabbing, positive, and calming response in the patient, so as to divert or distract or avert the attention of the patient away from visually and cognitively focusing on fluid transfers between the patient and the labelled medical device. Another example combination of images may comprise, for example, playful and cartoonish characterized images of kittens and puppies interacting with one another, perhaps interacting with each other relative to a toy of some kind. The choice of the beach ball and dinosaur images shown in FIG. 1A (and other figures) is not limiting and exemplary only, with the images reproduced in the present disclosure in black and white or greyscale, but are preferably in colors determined to evoke the desired attention grabbing and calming response (drawing the patient's attention away from the medical procedure being performed).

FIG. 1B illustrates a top view of a label or sticker 120 applicable onto medical devices or other object, whereby an area of non-transparent material 140 (with attention grabbing images thereon) is surrounded by areas of transparent material 138 along the perimeter (130, 134, 136, 132) of the non-transparent area 140, according to one embodiment. As for label 100 and its opaque area 116, the opaque/non-transparent area 140 of label 120 is preferably sized to cover a portion of a target medical device and leave uncovered measurement graduations and/or other information on the medical device. For application on a syringe body, the width 134-136 of the non-transparent portion 140 is less than the circumference of the target syringe and such that transparent portions between 126 and 134, between 128 and 136, between 122 and 130, and between 132 and 124 leave unobscured (uncovered) measurement graduation and/or other information of the target syringe body.

FIG. 1C illustrates a top view of a label or sticker 142 applicable onto medical devices or other object, whereby a strip of non-transparent material 154 (having attention grabbing images thereon) is side-by-side with an area of transparent material 152, according to one embodiment. As for the embodiments shown in FIGS. 1A and 1B, the non-transparent portion 154 of label 142 is preferably sized so as to obscure at least a portion of the target medical device (such as a target syringe) to achieve an attention grabbing, distraction of the patient's attention away from the medical procedure being performed, without covering or obscuring measure graduations or other information on the medical device that is helpful for effective operation of the medical device, with such measurement graduations or other information being visible even if covered by a portion of the transparent area/portion 152. For application on a syringe body, the width 150-153 of the non-transparent portion 154 is less than the circumference of the target syringe and such that transparent portions between 153 and 148 leave unobscured (uncovered) measurement graduation and/or other information of the target syringe body. The longitudinal length 144-146 of label 142 is preferably dimensioned as for the corresponding longitudinal length of label 100 shown in FIG. 1A.

FIG. 2A illustrates a cross-section of the label or sticker 100 shown in FIG. 1A, whereby the strip of non-transparent material 156 is on top of a layer of transparent material 158, or the strip of non-transparent material 156 is adjacent to areas of transparent material 158 on each of two parallel sides, with an adhesive layer as the bottom most layer and adapted to adhere to a target medical device surface, according to embodiments. The non-transparent material 156 may comprise, for example, ink printing on the transparent material 158 so as to at least partially render the printed portions to be at least in part non-transparent, or enough non-transparent to render the attention grabbing, kid-themed images to sufficiently obscure the patient's view of fluid within the target syringe or target medical device and/or to sufficiently obscure the patient's view of the plunger seal position and plunger seal movement within the target syringe body. In other embodiments, the non-transparent material 156 may comprise a separate layer from the transparent material 158, and may be above or below the transparent material 158; in each case, the adhesive material 160 comprises a bottom most face of the label, with such bottom most face adapted for adherence to the target medical device surface.

FIG. 2B illustrates a cross-section of the label or sticker 120 shown in FIG. 1B, whereby the area of non-transparent material 162 is on top of a layer of transparent material 164, or the area of non-transparent material 162 is set within areas of transparent material 164 about the perimeter of the area of non-transparent material 162, with an adhesive layer 166 as the bottom most layer and adapted to adhere to a target medical device surface, according to embodiments. And FIG. 2C illustrates a cross-section of the label or sticker 142 shown in FIG. 1C, whereby the strip of non-transparent material 168 is on top of a layer of transparent material 169, or the strip of non-transparent material 168 is adjacent to the area of transparent material 169, with an adhesive layer 170 as the bottom most layer and adapted to adhere to a target medical device surface, according to embodiments. In various embodiments, the non-transparent material 162, 168 in FIGS. 2B and 2C are as described for the non-transparent material 156 in FIG. 2A. Likewise, in various embodiments, the transparent material 164, 169 in FIGS. 2B and 2C are preferably as described for the transparent material 158 in FIG. 2A.

Moving now to FIGS. 3A and 3B, FIG. 3A shows a perspective view of a combination 300 of a label, or pre-cut label 302, positioned upon a label liner 304, which may be arranged in a sheet of multiple columns and rows or in a tape/reel manner, or otherwise, wherefrom individual labels 302 may be removed for subsequent application to a syringe body or other (target) medical device, according to embodiments. The label 302 is preferably any of the labels 100, 120, 142 previously described.

FIG. 3B shows a label tape 310, whereby labels comprise a continuous repeating pattern/sequence of graphic images 312, and whereby labels of varying length may be cut/ripped for subsequent application to syringes or other medical devices of differing longitudinal lengths, according to embodiments. The graphic images 312 preferably comprise the images as described with respect to FIG. 1A. The relative widths of the non-transparent portion 316 and transparent portions 314 and 318 may be as shown and described with respect to FIG. 1A, according to some embodiments. In one embodiment, the width of the non-transparent portion 316 is approximately 50% of the width 320 of the label tape 310, and the widths of the transparent portions 314 and 318, each adjacent to the non-transparent portion 316, is approximately 25% of the width 320 of the label tape 310. In another embodiment, the relative width of non-transparent and transparent portions may be as shown and described with respect to FIG. 1C; and in one embodiment, the widths of the non-transparent and transparent portions are each approximately 50% of the width 320 of the label tape 310.

Continuing now to FIG. 4, FIG. 4 illustrates a medical practitioner holding a syringe 400 with a label 401, similar to the label shown in FIG. 1A, in a position for adhering to the syringe such that the non-transparent portion 424 of the label is aligned (adjacent to the measurement graduations 420) so as not to obscure graduations running longitudinally lengthwise along the barrel (body) 406 of the syringe, according to embodiments. As shown, the syringe 400 comprises a needle 402, a syringe body (or barrel) 406 (having an outside barrel diameter 422 and within which the plunger and plunger seal 404 travels from an insertion end at the barrel flange (or T end) 412 to a plunger seal end of travel position nearest the needle and opposite the barrel flange), and volume markings (or measuring graduations) 420. The label 401, as shown positioned to be further applied to the syringe barrel, comprises an approximately rectangular label having a longitudinal length (along the syringe barrel) 410-408, and a non-transparent (opaque) portion having a width 414 between two transparent portions having widths 416 and 418. The non-transparent portion preferably extends longitudinally from the needle end of the barrel 410 (so as to partially obscure the plunger seal 404 when the seal is nearest the needle end of the barrel) toward the T-end (barrel flange) 412.

Next, FIG. 5 illustrates the medical practitioner holding the syringe 400 with the label fully applied to the syringe body (barrel) 406 and with the syringe barrel rotated (with respect to FIG. 4) to depict the non-transparent strip 424 of the label facing the viewer, so as to hide the interior of the syringe and so as to hide the position and movement of the plunger seal, according to embodiments.

FIG. 6 shows a medical practitioner holding a differently dimensioned syringe 600 having an applied label 608 comprising a label as shown in FIG. 1A or 1C, according to embodiments. The label 608 is shown applied to the barrel of the syringe extending from the needle end of the barrel at the plunger seal 610 longitudinally toward the barrel flange 604 and plunger flange 602. In one embodiment, the label 608 may comprise a label as in FIG. 1A or a label similar to that shown in FIGS. 4 and 5. When used by a medical practitioner to give a patient (such as child or non-adult patient), the attention grabbing graphics on a non-transparent portion of the label 608 provides a distraction from the medial procedure (such as giving an injection or drawing/collecting a blood sample). The images of, for example, a beach ball and dinosaur distracts the child patient from the fluid in the syringe and movement of the plunger seal, and at least some distraction from the needle of the syringe and the medical procedure being performed.

FIG. 7 shows a medical practitioner holding a vial 702 from which fluid 712 has been drawn into the interior volume of a syringe 700, whereby a label as in FIG. 1A or 1C is applied to the syringe body, thereby obscuring (in the area covered by the non-transparent portion 708 of the label) both the fluid 712 within the syringe and the position of the syringe plunger seal 714 and also leaving visible the measurement graduations 710 along the syringe barrel, according to embodiments.

In this way, the windowed label on the syringe barrel provides an attention getting distraction to the patient and permits the medical practitioner to easily view the measurement graduations, thereby facilitating effective use of the syringe for the medical procedure.

Although the present invention has been described with reference to preferred embodiments, numerous modifications and variations can be made and still fall within the scope of the invention. For example, increasing or decreasing the scale of the preferred embodiment or increasing the number of instances of the preferred embodiment will still fall within the scope of the invention.

FIGS. 1A, 1B, 1C, 2A, 2B, 2C, 3A, 4, 5, 6, and 7 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

Throughout this specification relative language such as the words 'about' and 'approximately' may be used. Unless otherwise specified or described, this language seeks to incorporate at least 10% variability to the specified number or range. That variability may be plus 10% or negative 10% of the particular number specified.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A medical device with label, comprising:
an intravenous (IV) bag having a front side, a back side, and a tube extending therefrom, with the front and/or back side comprising material through which a fluid contained in the IV bag is visible and the front and/or back side comprising graduations or measurement markings or indicia of the IV bag for use by a medical practitioner, the graduations or measurement markings comprising numbers or lines or line segments adapted for indicating a quantity of the fluid contained in or removed from the IV bag, and the indicia comprising one or more alphanumeric character corresponding to the graduations or measurement markings and/or the fluid and/or the IV bag; and
a label completely adhered to the front and/or back side of the IV bag so that an adhesive surface of the label that extends across an entire bottom surface of the label is adhered to the front and/or back side of the IV bag facing the adhesive surface, wherein no part of the label completely adhered to the IV bag extends away from the front and/or back side of the IV bag to which the label is adhered, the label having:
a non-transparent portion adapted to receive graphic images thereon so that the graphic images are viewable from an outward facing surface of the label opposite the adhesive surface of the label and so that the non-transparent portion with the graphic images thereon obscure at least a portion of the front or back side of the IV bag upon which the adhesive surface is secureably positioned;

at least one transparent portion adjacent to the non-transparent portion and having the adhesive surface of the label extending thereunder, and the at least one transparent portion adapted to permit viewing at least some measurement graduations or indicia of the IV bag upon which the adhesive surface is securably positioned; and the graphic images at least on the non-transparent portion, wherein the graphic images are kid-themed images only and free from textual or graphical instructions and free from textual representations, wherein the graphic images are free from warnings and warning information, wherein the graphic images are non-informational and non-instructional in content, wherein the graphic images include at least one color that is neither the color black nor the color white, and wherein the graphic images are adapted to both attract attention of a child patient to thereby distract attention of the child patient from fluids associated with the IV bag and a medical procedure being performed on the child patient by the medical practitioner and obscure the at least the portion of the IV bag upon which the non-transparent portion is securably positioned from view of the child patient.

2. The medical device with label of claim 1, wherein the non-transparent portion comprises a longitudinal non-transparent portion length and a non-transparent portion width, wherein each of the at least one transparent portion comprises a longitudinal transparent portion length and a transparent portion width, and wherein the label comprises the non-transparent portion oriented between two transparent portions, with the longitudinal transparent portion length of each of the two transparent portions being the same as the longitudinal non-transparent portion length.

3. The medical device with label of claim 1, wherein, in a top view of the label, the non-transparent portion comprises a rectangle-shaped non-transparent area positioned within a larger rectangle defining an outer perimeter of the label, the resulting label comprising the non-transparent portion surrounded by areas of transparent material of the at least one transparent portions.

4. The medical device with label of claim 1, wherein the non-transparent portion comprises a longitudinal non-transparent portion length and a non-transparent portion width, wherein the at least one transparent portion comprises a longitudinal transparent portion length and a transparent portion width, and wherein the label comprises the non-transparent portion oriented side-by-side with one transparent portion, with the longitudinal transparent portion length of the transparent portion being the same as the longitudinal non-transparent portion length.

5. The medical device with label of claim 1, wherein the non-transparent portion comprises an opaque or non-translucent material.

6. The medical device with label of claim 1, wherein the non-transparent portion comprises material having sufficient opacity to hide viewing contents of the IV bag.

7. The medical device with label of claim 1, wherein the patient is a non-adult or child, and wherein the graphic images on the non-transparent portion are adapted to attract the attention of the non-adult or child toward the graphic images.

8. The medical device with The label of claim 7, wherein the graphic images comprise kid/child-themed images adapted to distract the patient's attention away from fluids and/or hypodermic needles involved in the medical procedure and/or involved in use of the IV bag having the label affixed thereon.

9. The medical device with label of claim 1, wherein the label comprises, within the non-transparent portion, an opaque or non-transparent material layer, a clear or transparent or translucent material layer under the opaque or non-transparent material layer, and an adhesive material layer under the clear or transparent or translucent material layer, and wherein the label comprises, within the at least one transparent portion, the clear or transparent or translucent material layer and the adhesive material layer under the clear or transparent or translucent material layer.

* * * * *